United States Patent [19]

Turner et al.

[11] Patent Number: 4,898,816
[45] Date of Patent: Feb. 6, 1990

[54] MEDIATORS FOR BIOELECTROCHEMICAL CELLS TO TEST FOR MICROBIOLOGICAL ACTIVITY

[75] Inventors: Anthony P. F. Turner; Ann Swain; Graham Ramsay; Marco Cardosi; Bernard H. Schneider, all of Cranfield, England

[73] Assignee: Paul de la Pena Limited, Worcestershire, United Kingdom

[21] Appl. No.: 27,979

[22] Filed: Mar. 19, 1987

[30] Foreign Application Priority Data

Mar. 19, 1986 [GB] United Kingdom ............... 8606831
Nov. 25, 1986 [GB] United Kingdom ............... 8628166

[51] Int. Cl.$^4$ ............................................. C12Q 1/04
[52] U.S. Cl. ........................................ 435/34; 435/4; 435/39
[58] Field of Search .............................. 435/4, 34, 39

[56] References Cited

U.S. PATENT DOCUMENTS 4,224,125 9/1980 Nakamura et al.

FOREIGN PATENT DOCUMENTS 136362 10/1985 European Pat. Off.
2000805 7/1977 United Kingdom.

OTHER PUBLICATIONS

Shopes et al.,–Chem. Abst. vol. 104 (1986) p. 145, 720 K.
Miller et al., *Chemical Abstracts*, vol. 92, No. 13 (1980), p. 218, 105921d.
Varfolomeev et al., *Chemical Abstracts*, vol. 85, No. 25 (1976), p. 251, 188993h.
Wolff et al., *Chemical Abstracts*, vol. 83, No. 25 (1976), p. 205, 203897j.
Buchanan et al., *Bergey's Manual of Determinative Bacteriology*, 8th Edn., 1974, pp. 217, 436, 481, 505.

*Primary Examiner*—Sam Rosen
*Attorney, Agent, or Firm*—Larson and Taylor

[57] ABSTRACT 1,4-Benzoquinone can act as a mediator of electron transfer in bioelectrochemical cells for measuring microbiological activity in a sample. In combination with ferricyanide it can provide a surprisingly high level of mediator activity with many microorganisms, and a more even response when the sample may contain a mixture of microorganisms.

11 Claims, No Drawings

MEDIATORS FOR BIOELECTROCHEMICAL CELLS TO TEST FOR MICROBIOLOGICAL ACTIVITY

FIELD OF THE INVENTION

This invention relates to bioelectrochemical cells, for use in measuring microbiological activity in a sample.

BACKGROUND

In bioelectrochemical cells, especially for measuring bacterial activity, ferricyanide has been proposed as a mediator for electron transfer between the bacteria and the electrodes. 1,4-Benzoquinone is also known as a mediator of electron transfer. Different bacteria present different levels of response, and for example Pseudomonas species (e.g. *P. aeruginosa*) normally have a rather poor response compared with, say, *E. coli* using ferricyanide as mediator. Large differences in response from different microorganisms makes it difficult to relate the signal to the amount of microbiological activity, unless one is expecting a particular microorganism to predominate.

SUMMARY OF THE INVENTION

It has now been found that a ferricyanide and a 1,4-benzoquinone can exhibit an unexpectedly high level of mediator activity compared with ferricyanide alone, or even compared with 1,4-benzoquinone alone, whereas in some cases the response is not significantly higher, and can even be lower, than using the mediators separately. The effect is such that a more even response can normally be expected from general or non-specific microbiological activity using the cocktail of mediators; while a particularly enhanced response can be expected when testing for many individual microorganisms using the mediator cocktail.

DESCRIPTION OF PREFERRED EMBODIMENTS

The invention will be further illustrated by reference to the following examples.

EXAMPLE 1

Use of 1,4-benzoquinone and ferricyanide cocktail in a two electrode bioelectrochemical cell (BEC)

The BEC was set up at pH 7.0 in a sodium phosphate buffer. Benzoquinone was prepared at 25 mM concentration and ferricyanide at 250 mM concentration. Initially the *E. coli* (150 µl) BEC response using 500 µl ferricyanide was compared with that of 500 µl ferricyanide+500 µl benzoquinone added together as a cocktail. The results are shown in Table 1.

TABLE 1

Use of 1,4-benzoquinone + ferricyanide cocktail as an alternative mediator

150 µl *E. coli* 1.7 × 10⁹ org/ml

| Mediator | BEC response µA/min |
|---|---|
| ferricyanide (500 µl) | 0.15 |
| ferricyanide (500 µl) + benzoquinone (500 µl) | 1.1 |

*P. aeruginosa* 1.7 × 10¹⁰ org/ml

| Cell volume | BEC response |
|---|---|

TABLE 1-continued

Use of 1,4-benzoquinone + ferricyanide cocktail as an alternative mediator

| in BEC (µl) | Mediator | µA/min |
|---|---|---|
| 1000 | ferricyanide (500 µl) | 0.23 |
| 500 | ferricyanide (500 µl) | 0.13 |
| 1000 | ferricyanide (500 µl) + benzoquinone (500 µl) | off scale in 10 sec. |
| 500 | ferricyanide (500 µl) + benzoquinone (500 µl) | 20.33 |

From the foregoing it will be seen that the cocktail gave about a 7.5-fold enhancement over the ferricyanide alone for *E. coli*. This experiment was repeated using *P. aeruginosa*. In this case the cocktail gave about a 750-fold enhancement over the ferricyanide alone.

EXAMPLE 2

Further investigation of the cocktail of Example 1 was made. The response of the benzoquinone cocktail was compared with that of the two individual components. The results are shown in Table 2.

TABLE 2

Comparison of the BEC response of the benzoquinone cocktail with that of the two individual components
150 µl *P. aeruginosa* 1.2 × 10¹⁰ org/ml

| Mediator | BEC response µA/min |
|---|---|
| benzoquinone (500 µl) | 0.64 |
| benzoquinone (1000 µl) | 1.1 |
| benzoquinone (500 µl) + ferricyanide (500 µl) | 2.9 |
| ferricyanide (500 µl) | 0.06 |

These results showed that the rate of change of current with time obtained with the mediator cocktail was more than the sum of the slopes of the individual components. In this case the cocktail gave a 48-fold enhancement over ferricyanide alone.

EXAMPLE 3

It was noted that the BEC response using 1 ml of benzoquinone was greater than that using 0.5 ml; therefore the concentration of benzoquinone relative to ferricyanide was increased in an attempt to further enhance the BEC response. The results are shown in Table 3.

TABLE 3

Effect of varying benzoquinone concentration in the cocktail on the BEC response
150 µl *P. aeruginosa* 1.2 × 10¹⁰ org/ml

| Mediator | BEC response µA/min |
|---|---|
| benzoquinone (1000 µl) | 0.88 |
| benzoquinone (1000 µl) + ferricyanide (500 µl) | 1.22 |
| benzoquinone (500 µl) + ferricyanide (500 µl) | 1.37 |
| ferricyanide (500 µl) | 0.09 |

It will be seen that increasing the relative amount of benzoquinone in the mediator cocktail did not further enhance the BEC response. 1 ml Benzoquinone+500 µl ferricyanide produced a 13.6-fold enhancement of the response whereas 500 µl benzoquinone+500 µl ferricyanide resulted in a 15.2-fold enhancement.

EXAMPLE 4

The effect of the mediator cocktail with a variety of bacteria

The bacteria to be examined were grown up overnight, and then tested in a BEC using the following composition:

|  |  |  |
|---|---|---|
|  | 150 μl | Glucose (25 mM) |
|  | 500 μl | Bacterial suspension |
| Mediator: |  |  |
| (i) | 250 μl | Ferricyanide (250 mM), or |
| (ii) | 250 μl | Benzoquinone (25 mM), or |
| (iii) | 250 μl | Ferricyanide (250 mM) + |
|  | 250 μl | Benzoquinone (25 mM). |

Sodium phosphate buffer (50 mM, pH 7.0) containing KCl (to a final concentration of 100 mM in the BEC) to a final BEC volume of 10 ml.

The work was carried out at 30° C. using a platinum working electrode and a silver/silver chloride reference electrode.

The results were obtained as mean values of a minimum of four runs. The standard BEC solution was prepared and the response was observed with each of the three mediator combinations given above. The results are shown in Table 4.

TABLE 4

| | Measured Rates | | |
|---|---|---|---|
| | FERRI-CYANIDE | BENZO-QUINONE | COCK-TAIL |
| ORGANISM | (%) (a) | (%) (a) | (%) (b) |
| Acinetobacter | 8.3 | 44.4 | 189.8 |
| Agrobacterium tumefaciens | 208.5 | 36.9 | 32.4 |
| Alcaligenes faecalis | 80.4 | 47.5 | 78.1 |
| Bacillus licheniformis | 176.7 | 65.1 | 41.3 |
| Bacillus megaterium | 205.7 | 67.9 | 36.6 |
| Escherichia coli | 6.2 | 41.1 | 211.2 |
| Micrococcus lysodeikticus | 2.4 | 85.6 | 113.6 |
| Pseudomonas aeruginosa | 0.6 | 61.4 | 161.4 |
| Pseudomonas fluorescens | 4.5 | 122.6 | 78.7 |
| Staphylococcus aureus | 18.3 | 70.6 | 112.5 |
| Streptococcus faecalis | 4.7 | 79.8 | 118.2 |

(a):rate as % of cocktail response
(b):cocktail rate as % of response of both mediators combined Table 4 was compiled from measured data, examples of which are shown in Table 5.

TABLE 5

| Organism at | BEC RESPONSE (μA/min) | |
|---|---|---|
| $1 \times 10^9$/ml | Cocktail | Ferricyanide |
| Escherichia coli | 8.57 | 0.53 |
| Bacillus licheniformis | 0.75 | 1.33 |
| Pseudomonas aeruginosa | 1.39 | 0.007 |
| Total variation in relative responses | 11-fold | 200-fold |

The Table 5 data include E. coli, which is the best responder with the cocktail (out of those tested), P. aeruginosa, which is the poorest responder with ferricyanide alone, and B. licheniformis, a strain whose response is decreased with the cocktail relative to ferricyanide alone. It will be seen that the cocktail has greatly evened out the response of a mixed culture at a given concentration.

Tables 6 and 7 illustrate the effect of varying the relative concentrations of the two mediator components.

TABLE 6

| BENZOQUINONE CONCENTRATION (μM) | BEC RESPONSE (μA/min) |
|---|---|
| 250 | 3.95 |
| 100 | 1.05 |
| 25 | 0.74 |
| 2.5 | 0.58 |
| Ferricyanide concentration: | 2.5 mM |
| Sample: | $5 \times 10^6$ org/ml E. coli |

TABLE 7

| COCKTAIL COMPOSITION | | |
|---|---|---|
| FERRICYANIDE (mM) | BENZOQUINONE (mM) | BEC RESPONSE (μA/min) |
| 12.5 | 1.25 | 10.70 |
| 12.5 | 0.25 | 10.62 |
| 6.25 | 0.625 | 11.70 |
| 2.5 | 1.875 | 10.67 |
| 1.0 | 1.25 | 9.98 |

Sample: P. aeruginosa $5 \times 10^8$ org/ml

In Table 6, with E. coli, the ferricyanide:benzoquinone ratio varies from 1000:1 to 10:1 with only a sevenfold change in signal. In Table 7, with P. aeruginosa, that ratio varies from 50:1 to 0.8:1 with virtually no change in signal. The ratios therefore do not appear to be critical. Likewise the overall concentrations of the mediators does not seem to be critical, and can be lower than those exemplified, especially with the more sensitive microorganisms. We have further demonstrated above, the use of the mediator cocktail with examples of gram positive and gram negative bacteria, motile and non-motile organisms, rods and cocci.

We claim:

1. In a bioelectrochemical cell for use in measuring microbiological activity in a liquid sample suspected of containing microorganisms, wherein microbiological activity results in a mediator transfer of electrons between liquid and electrode in the cell and a consequent electrical signal is detected and measured, the improvement which comprises incorporating in the cell an amount of a ferricyanide and a 1,4-benzoquinone effective for said mediation of electron transfer.

2. A method for testing for microbiological activity in a sample suspected of containing microorganisms, which comprises measuring an electrical signal from a bioelectrochemical cell containing the sample in liquid form, the cell incorporating an amount of a ferricyanide and 1,4-benzoquinone effective for mediation of electron transfer between liquid and electrode.

3. A method according to claim 2 wherein the microorganisms comprise gram positive bacteria.

4. A method according to claim 2 wherein the microorganisms comprise gram negative bacteria.

5. A method according to claim 2 wherein the microorganisms comprise E. coli.

6. A method according to claim 2 wherein the microorganisms comprise Pseudomonas aeruginosa.

7. A method according to claim 2 wherein the microorganisms comprise Micrococcus lysodeikticus.

8. A method according to claim 2 wherein the microorganisms comprise Staphylococcus aureus.

9. A method according to claim 2 wherein the microorganisms comprise Streptococcus faecalis.

10. A method according to claim 2 wherein the microorganisms comprise Acinetobacter.

11. A method according to claim 2 wherein the sample contains a mixture of different species of genera of microorganism.

* * * * *